(12) United States Patent
Feferberg

(10) Patent No.: US 9,345,909 B2
(45) Date of Patent: May 24, 2016

(54) SKIN ULCER TREATMENT

(76) Inventor: Ilan Feferberg, Rishon LeZion (IL)

( * ) Notice: Subject to any disclaimer, the term of this patent is extended or adjusted under 35 U.S.C. 154(b) by 239 days.

(21) Appl. No.: 13/978,682

(22) PCT Filed: Dec. 22, 2011

(86) PCT No.: PCT/IL2011/050072
§ 371 (c)(1),
(2), (4) Date: Jul. 8, 2013

(87) PCT Pub. No.: WO2012/085920
PCT Pub. Date: Jun. 28, 2012

(65) Prior Publication Data
US 2013/0289416 A1    Oct. 31, 2013

Related U.S. Application Data

(60) Provisional application No. 61/425,807, filed on Dec. 22, 2010.

(51) Int. Cl.
*A61B 8/00*     (2006.01)
*A61N 7/00*     (2006.01)
*A61N 1/04*     (2006.01)
(Continued)

(52) U.S. Cl.
CPC ............... *A61N 7/00* (2013.01); *A61B 5/0077* (2013.01); *A61N 1/0468* (2013.01); *A61N 1/326* (2013.01); *A61N 2007/0017* (2013.01); *A61N 2007/0073* (2013.01)

(58) Field of Classification Search
CPC ..................... A61B 5/0077; A61B 2007/0017; A61N 1/0468; A61N 1/326; A61N 2007/0073; A61N 7/00

USPC ..................... 600/439–463, 373–383
See application file for complete search history.

(56) References Cited

U.S. PATENT DOCUMENTS 7,563,224 B2    7/2009   Puchek
7,914,469 B2    3/2011   Torbati
(Continued)

FOREIGN PATENT DOCUMENTS

WO    2004080147 A2    9/2004
WO    2008002773 A2    1/2008
(Continued)

OTHER PUBLICATIONS

International Search Report mailed May 2, 2012 for PCT/IL2011/50072.

(Continued)

*Primary Examiner* — Sanjay Cattungal
(74) *Attorney, Agent, or Firm* — Paul D. Bianco; Katharine Davis; Fleit Gibbons Gutman Bongini & Bianco PL

(57) ABSTRACT

A system and method for facilitating the healing of a skin ulcer, such as a diabetic ulcer, on a treatment region of a body. Ultrasound waves are transmitted to the treatment region. Interferential electrical stimulation is applied to the treatment region, simultaneously with the ultrasound transmission. The treatment region may be massaged with a massaging device during the treatment session. A gel may be applied onto the treatment region to facilitate the ultrasound transmission and electrical stimulation. A measurement system may be used to obtain accurate measurements of the skin ulcer, to provide a quantitative determination of the healing progression.

6 Claims, 7 Drawing Sheets

(51) Int. Cl.
*A61N 1/32* (2006.01)
*A61B 5/00* (2006.01)

(56) References Cited

U.S. PATENT DOCUMENTS

| | | | | |
|---|---|---|---|---|
| 2002/0193784 A1* | 12/2002 | McHale | ............ | A61K 41/00 606/27 |
| 2003/0004556 A1* | 1/2003 | McDaniel | ............ | A61K 8/494 607/88 |
| 2004/0236268 A1* | 11/2004 | Mitragotri | ............ | A61B 5/411 604/20 |
| 2004/0260210 A1* | 12/2004 | Ella | ............ | A61H 7/008 601/7 |
| 2005/0049543 A1* | 3/2005 | Anderson | ............ | A61B 18/14 604/20 |
| 2007/0027411 A1* | 2/2007 | Ella | ............ | A61H 7/008 601/7 |
| 2007/0055154 A1* | 3/2007 | Torbati | ............ | A61H 23/0245 600/439 |
| 2007/0299369 A1 | 12/2007 | Babaev | | |
| 2008/0125617 A1 | 5/2008 | Puchek | | |
| 2009/0043293 A1 | 2/2009 | Pankratov et al. | | |
| 2010/0049262 A1 | 2/2010 | Puchek | | |
| 2010/0145399 A1 | 6/2010 | Johari | | |
| 2010/0198064 A1 | 8/2010 | Perl et al. | | |
| 2010/0222734 A1* | 9/2010 | Jayes | ............ | A61N 1/0492 604/20 |
| 2012/0150163 A1* | 6/2012 | Neev | ............ | A61B 18/08 606/9 |
| 2013/0012840 A1 | 1/2013 | Feferberg | | |

FOREIGN PATENT DOCUMENTS

| | | |
|---|---|---|
| WO | 2008061390 A1 | 5/2008 |
| WO | 2008064272 A2 | 5/2008 |
| WO | 2008099376 A2 | 8/2008 |
| WO | 2009023568 A1 | 2/2009 |
| WO | 2009109196 A1 | 9/2009 |
| WO | 2011117869 A1 | 9/2011 |

OTHER PUBLICATIONS

International Preliminary Report published Jun. 25, 2013 for PCT/IL2011/50072.
Written Opinion published Jun. 22, 2013 for PCT/IL2011/50072.

* cited by examiner

SKIN ULCER TREATMENT

FIELD OF THE DISCLOSED TECHNIQUE

The disclosed technique relates to systems and methods of treating skin ulcers, particularly severe diabetic ulcers.

BACKGROUND OF THE DISCLOSED TECHNIQUE

Diabetes Mellitus, typically referred to as simply "diabetes", is a common disease that afflicts numerous individuals worldwide. One complication associated with diabetes is the appearance of skin ulcers or sores, typically occurring in the feet or legs. Diabetic ulcers often initiate as blisters or lesions, developing into inflammation, discoloration and fissures of outer skin tissue. A diabetic ulcer may progress into necrosis of deeper skin layers, which in severe cases may extend into muscle and even bone loss and may eventually necessitate amputation. Diabetic ulcers generally occur as a result of arterial blockages and peripheral nerve damage (neuropathy). Another type of skin ulcers are "decubitus ulcers", also known as "bedsores" or "pressure sores", which develop as a result of prolonged pressure being applied against a body region that serves to cut off circulation and preventing adequate blood supply to the skin tissue, frequently due to sitting or lying down for too long in the same position. Decubitus ulcers are a common problem for nursing home residents and other bedridden patients, necessitating their shifting positions at regular intervals to ensure proper blood circulation in the pressured body regions.

Wounds and skin ulcers, such as diabetic sores and decubitus ulcers, can be extremely painful, and usually severely degrade the quality of life of the affected individual. In addition, such skin ulcers tend to be difficult to treat. In many cases, the body is ostensibly unable to recuperate from these wounds on its own. Various treatment methods are known in the art, however, these treatments tend to be difficult, time-consuming, expensive, and not always effective.

U.S. Patent Application No. 2010/0049262, to Puchek, entitled "Method of treating a severe diabetic ulcer", discloses a method specifically designed to treat a severe diabetic ulcer that penetrates the subcutaneous fat layer of a diabetic patient. The method comprises the steps of: administering a treatment session comprising at least three pulsed electromagnetic fields (PEMF) applications, PEMF applications 1, 2, and 3, and at least two intermittent compression therapy (ICT) applications. The PEMF application and ICT therapy settings address specific factors that are necessary to induce healing of the diabetic ulcer and prevent amputation. A dressing having a silver and/or honey anti-infection composition may be applied to the ulcer area to inhibit microbial growth. Ultrasound may be applied to the ulcer area for a time sufficient to inhibit microbial growth.

PCT Patent Application No. WO2008/002773 to Babaev, entitled "Ultrasound wound care device and method", discloses an ultrasound device method for treating wounds. The ultrasound wound care device comprises a generator, an ultrasound transducer, an ultrasound horn, and a cavitation chamber. The device may further comprise a fluid, non-atomized, coupling medium. Ultrasound entering the cavitation chamber induces cavitations within the coupling medium, providing therapeutic benefits to the wound being treated. The ultrasound entering the cavitation chamber is also transmitted through the coupling medium to the wound, providing direct therapeutic benefits to the wound.

SUMMARY OF THE DISCLOSED TECHNIQUE

In accordance with one aspect of the disclosed technique, there is thus provided a system for facilitating the healing of a skin ulcer on a treatment region of a body. The system includes an ultrasound apparatus and an electrical stimulation apparatus. The ultrasound apparatus transmits ultrasound waves to the treatment region. The electrical stimulation apparatus applies interferential electrical stimulation to the treatment region, simultaneously with the transmission of ultrasound waves. The skin ulcer may be a diabetic ulcer. The system may include a massaging device, for massaging the treatment region. A gel may be applied to the treatment region, to facilitate the transmission of the ultrasound waves and the application of the interferential electrical stimulation. The operating intensity of the ultrasound waves is between 0.5 W/cm$^2$ and 3 W/cm$^2$. The operating frequency of the ultrasound waves is between 1 MHz and 4 MHz. The operating intensity of the ultrasound waves may be varied during a treatment session. The operating frequency of the interferential electrical stimulation is between 5 Hz and 150 Hz. The operating intensity of the interferential electrical stimulation is between 5 mA and 90 mA. The alternating currents of the interferential electrical stimulation may include adjustable parameters, such as: a frequency parameter; an amplitude modulated frequency parameter; a spectrum parameter; a rotation parameter; an emission parameter; and a pause parameter. The interferential electrical stimulation may be: premodulated; biphasic; interferential (I/F) isoplanar (4 poles); interferential (I/F) vectorial (4 poles); medium frequency (M/F)' or any combination thereof. The electrical stimulation apparatus may cycle through multiple interferential electrical stimulation techniques during a treatment session. The operating frequency of the interferential electrical stimulation may be varied during a treatment session. The operating frequency of the interferential electrical stimulation may be varied in accordance with a predetermined pattern, such as: applying a first frequency for a fixed amount of time before switching to a second frequency; gradually changing frequencies from a first frequency to a second frequency over various time durations; and intermittently applying extreme frequencies within the frequency range. The system may include a measurement system. The measurement system includes a camera, a reference measurement ruler, and a processor. The camera images the skin ulcer. The reference measurement ruler is positioned adjacent to the skin ulcer while the camera images the skin ulcer. The processor calculates at least one measurement of the surface area of a region associated with the skin ulcer, based on a comparative reference scale established using the reference measurement ruler.

In accordance with another aspect of the disclosed technique, there is also provided a method for facilitating the healing of a skin ulcer on a treatment region of a body. The method includes the procedures of transmitting ultrasound waves to the treatment region, and applying interferential electrical stimulation to the treatment region, simultaneously with the transmission of said ultrasound waves. The skin ulcer may be a diabetic ulcer. The method may further include the procedure of massaging the treatment region. The method may further include the procedure of applying a gel to the treatment region, to facilitate the transmission of the ultrasound waves and the application of the interferential electrical stimulation. The operating intensity of the ultrasound waves is between 0.5 W/cm² and 3 W/cm². The operating frequency of the ultrasound waves is between 1 MHz and 4 MHz. The operating intensity of the ultrasound waves may be varied during a treatment session. The operating frequency of the interferential electrical stimulation is between 5 Hz and 150 Hz. The operating intensity of the interferential electrical stimulation is between 5 mA and 90 mA. The alternating currents of the interferential electrical stimulation may include adjustable parameters, such as: a frequency parameter; an amplitude modulated frequency parameter; a spectrum parameter; a rotation parameter; an emission parameter; and a pause parameter. The interferential electrical stimulation may be: premodulated; biphasic; interferential (I/F) isoplanar (4 poles); interferential (I/F) vectorial (4 poles); medium frequency (M/F); or any combination thereof. The electrical stimulation apparatus may cycle through multiple interferential electrical stimulation techniques during a treatment session. The operating frequency of the interferential electrical stimulation may be varied during a treatment session. The operating frequency of the interferential electrical stimulation may be varied in accordance with a predetermined pattern, such as: applying a first frequency for a fixed amount of time before switching to a second frequency; gradually changing frequencies from a first frequency to a second frequency over various time durations; and intermittently applying extreme frequencies within the frequency range. The method may further include the procedure of measuring the skin ulcer. The procedure of measuring the skin ulcer includes the procedures of positioning a reference measurement ruler adjacent to the skin ulcer; imaging the skin ulcer and the reference measurement ruler; and calculating at least one measurement of the surface area of a region associated with the skin ulcer, based on a comparative reference scale established using the reference measurement ruler.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art by providing a novel system and method for facilitating the healing of skin ulcers, particularly diabetic ulcers and decubitus ulcers. The system includes an ultrasound apparatus configured to transmit ultrasound waves, at a particular frequency range and intensity range, toward the treatment region. The ultrasound transmission induces the release of fluids and waste products in the underlying tissues, and their subsequent removal from the circulatory system, and improves microcirculation at the treatment region. The system further includes an electrical stimulation apparatus for providing interferential electrical stimulation to the treatment region, simultaneously with the ultrasound transmission. The interferential electrical stimulation induces intermittent contractions of the muscle tissue at the treatment region, which applies repetitive pressure against the underlying tissues and associated vasculature from below the skin ulcer, promoting blood flow and improved circulation. An external massage may also be applied at the treatment region, such as by using a massaging device or manual manipulation, to further promote blood flow and improve circulatory and lymphatic operation in the region. Additional pressure may be exerted by kneading or pressing the ultrasound transducer against the treatment region.

The term "skin ulcer", and any variations thereof, as used herein refers to any type of sore, wound, lesion, and the like, on at least a skin tissue region of a body, and which may extend further into subcutaneous tissue. Accordingly, the disclosed technique is applicable for treating any type or form of skin ulcers, of any size, shape, or degree of severity.

The term "simultaneous", and any variations thereof, as used herein, also encompasses a period of time before, and a period of time after, the duration under consideration. Accordingly, a first procedure that is described as being performed "simultaneously" to a second procedure, may be performed, e.g., immediately before, immediately after, and/or during the second procedure.

Figure 1:
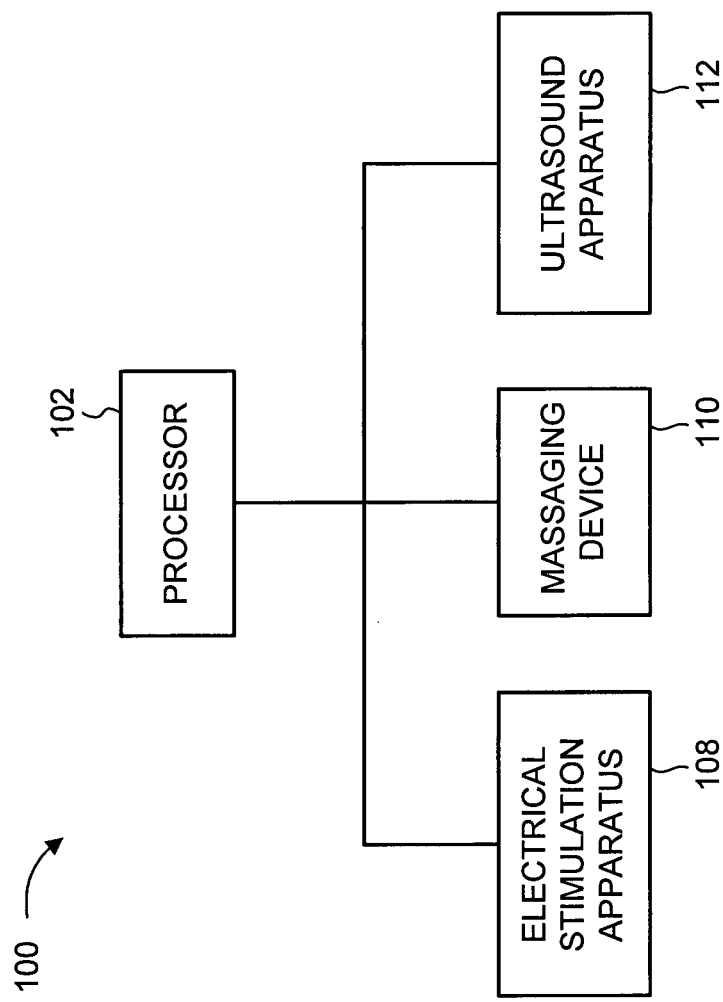
FIG. 1 is a block diagram of a system for facilitating the healing of a skin ulcer, constructed and operative in accordance with an embodiment of the disclosed technique.
Figure 2:
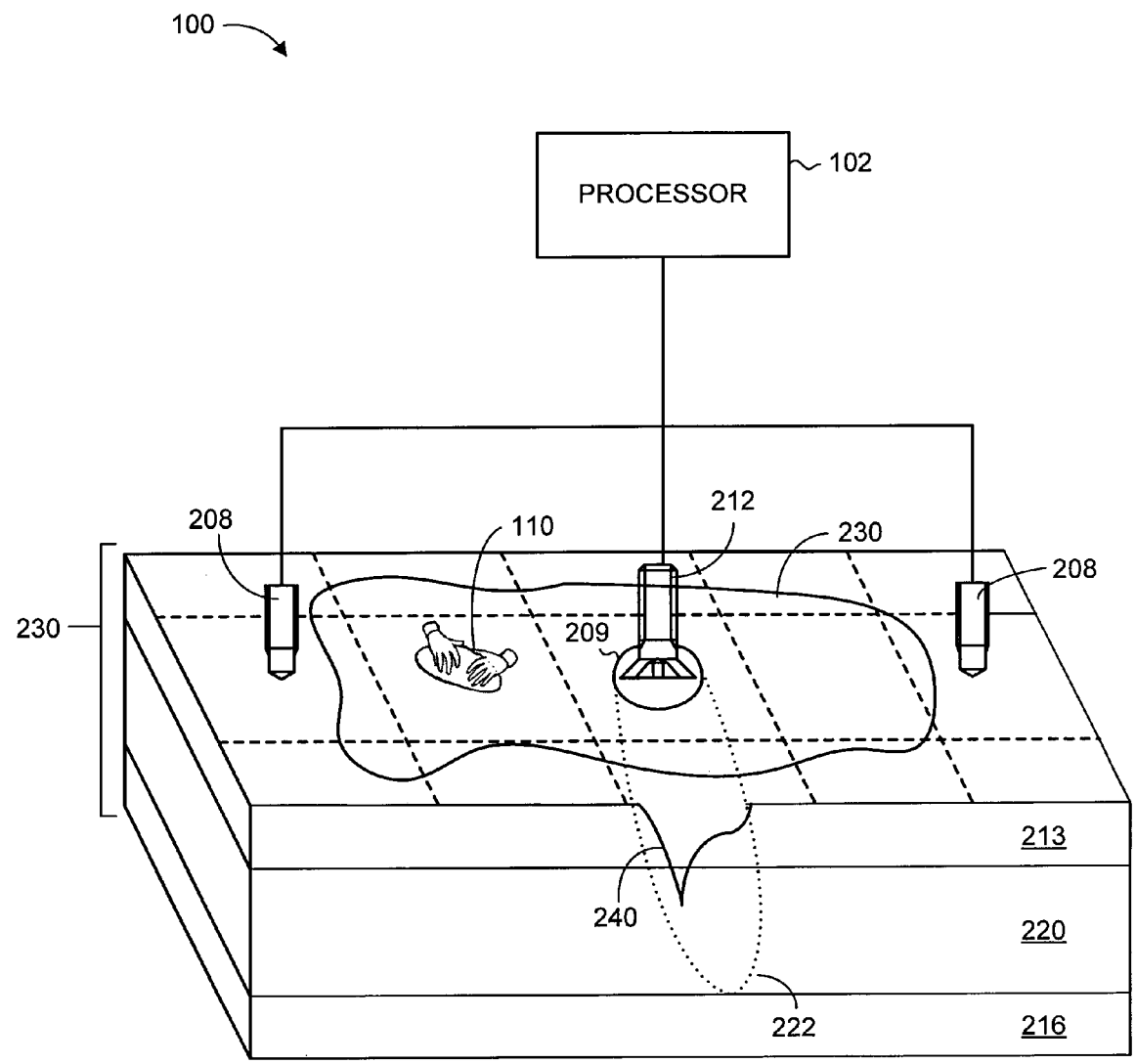
FIG. 2 is a schematic illustration of the system of FIG. 1 treating a body region of a patient, in accordance with an embodiment of the disclosed technique.

Reference is now made to FIGS. 1 and 2. FIG. 1 is a block diagram of a system, generally referenced 100, for facilitating the healing of a skin ulcer, constructed and operative in accordance with an embodiment of the disclosed technique. FIG. 2 is a schematic illustration of the system of FIG. 1 treating a body region of a patient, in accordance with an embodiment of the disclosed technique. System 100 includes a processor 102, an ultrasound apparatus 112, an electrical stimulation apparatus 108 and a massaging device 110. Processor 102 is coupled with electrical stimulation apparatus 108, with massaging device 110, and with ultrasound apparatus 112. Electrical stimulation apparatus 108 includes electrodes 208. Ultrasound apparatus 112 typically includes a signal generator unit (not shown) and an ultrasound transducer 212. Processor 102 is operative to control and manage the operations of electrical stimulation apparatus 108, massaging device 110, and ultrasound apparatus 112. Processor 102 may be partially or fully embodied by any form of hardware, software, or a combination thereof, and may be at least partially embodied by a hardware or software component that is integrated with any one of: electrical stimulation apparatus 108, massaging device 110, and ultrasound apparatus 112.

Referring to FIG. 2, system 100 is applied to a treatment region 230 on the body of a patient, where treatment region 230 includes a skin ulcer 240 that requires treatment. Skin ulcer 240 is, for example, a diabetic foot ulcer. Treatment region 230 includes a skin tissue layer 213 (i.e., epidermis, dermis, and hypodermis), a fat tissue layer 220 (i.e., subcutaneous fat), and a muscle tissue layer 216. Skin ulcer 240 may penetrate deep into the skin tissue layer 213 and fat tissue layer 220, and may even extend into muscle tissue layer 216 in severe circumstances.

Electrodes 208 are positioned onto the patient at treatment region 230 in proximity to skin ulcer 240. Stimulation apparatus 108 applies interferential electrical stimulation to treatment region 230 via electrodes 208. The electrical stimulation reaches muscle tissue 216 and produces a pressing or squeezing action from below skin ulcer 240 while stimulating blood circulation in the area, which serves to promote the healing process of skin ulcer 240. Electrodes 208 may be adhered or otherwise fixedly positioned directly onto skin layer 213, such that electrodes 208 remain stationary during treatment. Alternatively, electrodes 208 may be integrated with ultrasound transducer 212 such that electrodes 208 are moved and operated in conjunction with transducer 212.

Ultrasound transducer 212 transmits ultrasound waves toward treatment region 230. A gel 209 is optionally applied to the treatment region, to enhance the penetration of the ultrasound waves, as elaborated upon hereinbelow. The transmitted ultrasound waves penetrate at least skin tissue layer 213 and fat tissue layer 220. The intensity and/or frequency of the transmitted ultrasound waves may be selected so that the ultrasound waves are sufficiently attenuated while propagating through treatment region 230, in order to prevent adverse effects that could result if the ultrasound waves reach muscle tissue layer 216 (e.g., causing a painful sensation, and/or harming healthy tissue). Alternatively, the ultrasound waves may nevertheless be allowed to penetrate into muscle tissue layer 216. A typical cross-section of effective ultrasound penetration in accordance with the disclosed technique is represented by perforated lines 222. In general, the transmitted ultrasound waves function to sufficiently stimulate blood circulation in the tissue layers of treatment region 130, thereby promoting the healing of skin ulcer 240. Ultrasound transducer 212 is preferably operative to knead or press against the skin at treatment region 230 during the operation of ultrasound apparatus 112. Massaging device 110 massages treatment region 230, preferably simultaneously with the electrical stimulation and the ultrasound transmission.

Figure 3:
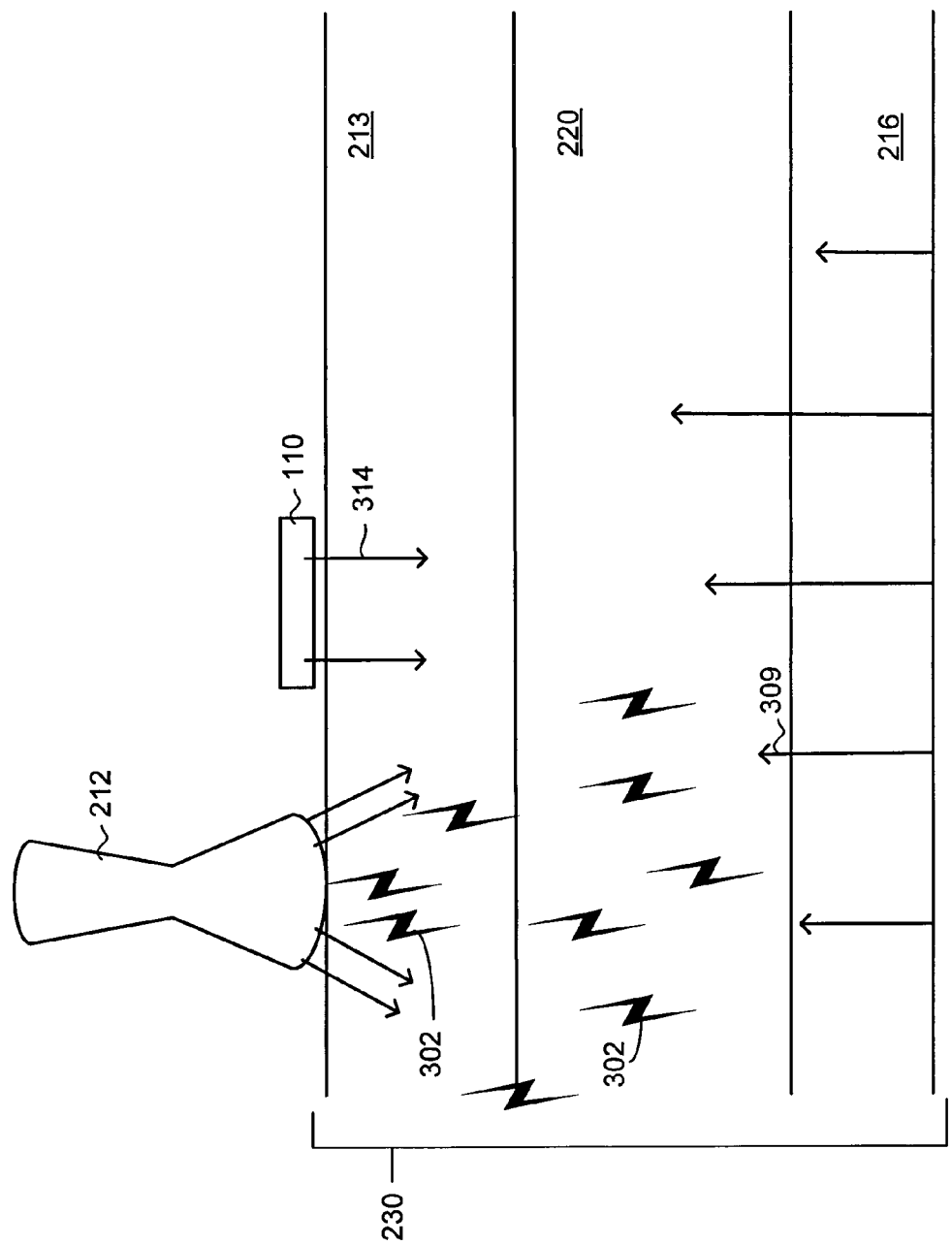
FIG. 3 is a schematic illustration of physical and biological processes that occur during the application of the disclosed technique.

Reference is now made to FIG. 3, which is a schematic illustration of physical and biological processes that occur during the application of the disclosed technique. Ultrasound transducer 212 transmits ultrasound waves 302 toward treatment region 230. Ultrasound waves are very high frequency sound waves (i.e., above approximately 20 KHz) that create changes in the density and pressure of the medium through which the waves propagate. Ultrasound waves are longitudinal waves made up of high pressure regions ("compression") and low pressure regions ("rarefaction"). When an ultrasound wave strikes a material, the particles of that material begin to oscillate and gradually generate heat. Thus, kinetic energy from the ultrasound wave is transferred into thermal energy in the impacted material.

One effect of the ultrasound transmission is to improve microcirculation (i.e., the blood circulation through the microvascular network that is responsible for the distribution of blood within tissues) in the treatment region. As ultrasound waves 302 propagate through skin tissue layer 213 and fat tissue layer 220, the resultant oscillation and softening of the tissues generates heat and pressure, which induces the release and subsequent removal of fluids and waste products stored in the tissue, while also enhancing blood flow and circulation in the region.

In accordance with the disclosed technique, ultrasound transducer 212 emits ultrasound waves 302 at a frequency between approximately 1-4 MHz, and at intensities varying between approximately 0.5-3 W/cm$^2$, preferably between 1.5-2.5 W/cm$^2$, further preferably between 1.8-2.25 W/cm$^2$, and yet further preferably at approximately 2 W/cm$^2$. At these operating ranges, it is conjectured that microcirculation improvement takes place in the skin tissue and fat tissue in proximity to the treatment region, while deeper healthy tissues, such as muscles, remain unharmed. The ultrasound operating frequency or operating intensity may be varied over the course of a treatment session. Varying the operating frequency allows targeting of different depths in treatment region 230. Particularly, higher frequencies may be used to reach shallower tissue layers (e.g., skin tissue), whereas lower frequencies may be used to reach deeper tissue layers (e.g., fat tissue). When varying the frequency with regards to the depth of region being targeted, a first depth is preferably first treated completely, followed by the treatment of a second depth. The ultrasound intensity may be varied independent of the ultrasound frequency. Preferably, the operating frequency of ultrasound transducer 212 remains between 1-3 MHz, and the operating intensity of ultrasound transducer 212 remains between 1.5-2.1 W/cm$^2$. Different frequency/intensity combinations (e.g., high frequency and high intensity, low frequency and low intensity, high frequency and low intensity, low frequency and high intensity) may be applied in order to produce a desired effect and/or to penetrate a desired depth of the treatment region.

The treatment provider preferably utilizes feedback from the patient while the treatment is taking place, and proceeds to adjust the treatment if necessary. For example, the transmitted ultrasound waves are applied at a specific intensity until the patient experiences pain or can no longer endure the pain. If the patient indicates that he/she is experiencing pain or discomfort, the treatment provider may reduce the ultrasound intensity, reposition the ultrasound transducer onto a different portion of the treatment region, and/or change the ultrasound frequency in order to reach a different depth of the treatment region.

Figure 4A:
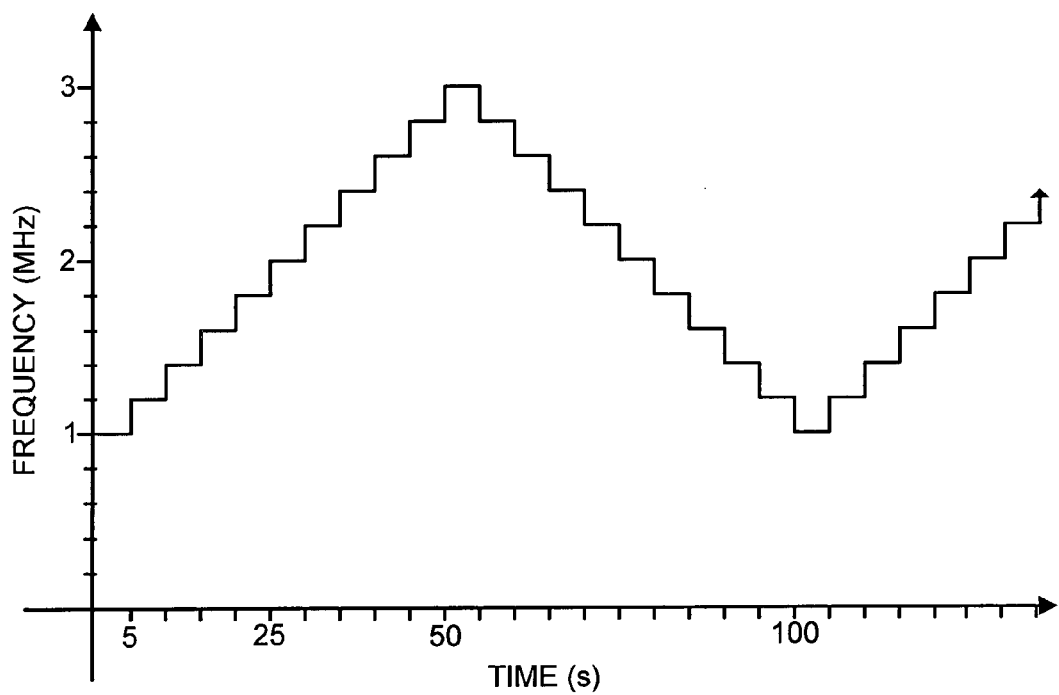
FIG. 4A is a graph that depicts a first exemplary variation of ultrasound frequency as a function of time, in accordance with an embodiment of the disclosed technique.
Figure 4B:
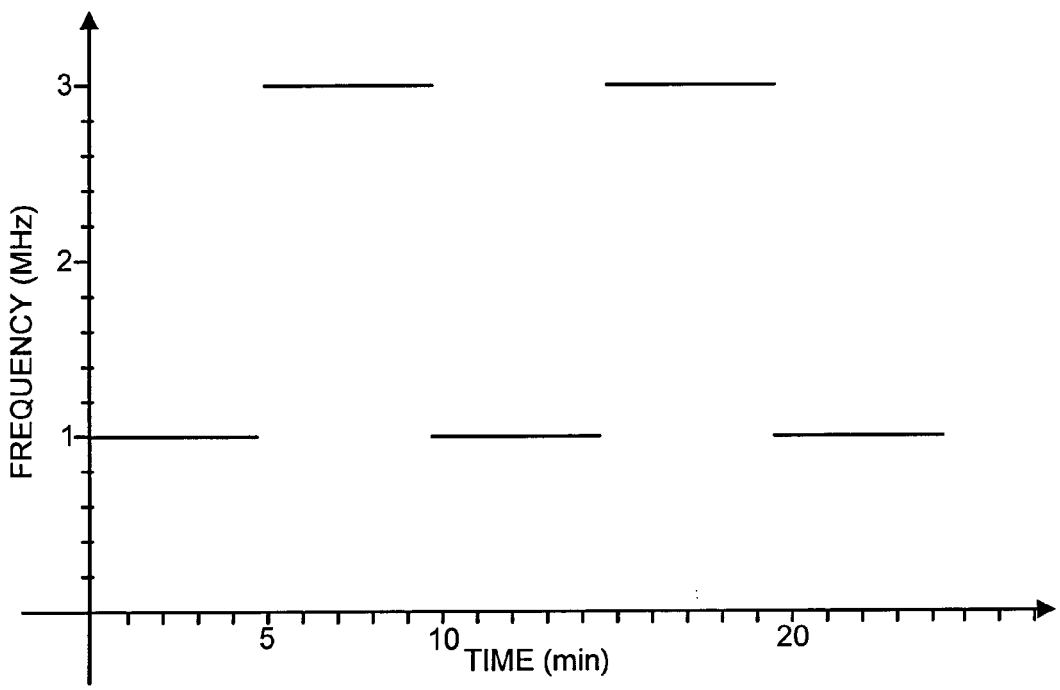
FIG. 4B is a graph that depicts a second exemplary variation of ultrasound frequency as a function of time, in accordance with an embodiment of the disclosed technique.

Reference is now made to FIGS. 4A and 4B. FIG. 4A is a graph that depicts a first exemplary variation of ultrasound frequency as a function of time, in accordance with an embodiment of the disclosed technique. FIG. 4B is a graph that depicts a second exemplary variation of ultrasound frequency as a function of time, in accordance with an embodiment of the disclosed technique. Referring to FIG. 4A, the frequency can be altered over the course of the treatment from 1 MHz to 3 MHz and back again to 1 MHz, cyclically, at 200 KHz increments lasting 5 seconds. The increments may alternatively be shorter or longer time periods, for example 3 seconds or 10 seconds, and may alternatively be larger or smaller frequencies, for example 100 KHz or 500 KHz. Referring to FIG. 4B, the frequency can also be altered sharply, in a stepwise manner, between 1 MHz and 3 MHz and back again to 1 MHz, cyclically, where a particular frequency is applied for 5 minutes. The duration of the applied frequency may alternatively be a shorter or longer time period, for example 3 minutes, 10 minutes, or 20 minutes.

Referring back to FIGS. 1 and 2, stimulation apparatus 108 applies interferential electrical stimulation to treatment region 230, inducing intermittent contractions of muscle tissue layer 216. Electrodes 208 are attached to skin tissue layer 213 with the aid of attaching means, such as adhesive patches, at the beginning and end of the muscle fibers that cross treatment region 230. Typically, at least two pairs of electrodes 208 are employed to generate interferential beat frequencies, as will be discussed further hereinbelow. Interferential current is applied to treatment region 230 via electrodes 208 at frequencies ranging from 5-150 Hz resultant beat frequency, which stimulates intermittent contractions of the muscle tissue. These contractions create a tense bedding of muscle against fat tissue layer 220 and skin tissue layer 213 around skin ulcer 240, providing an opposing force against the treated surface tissue. The rapid contraction-relaxation motion of the muscles (represented by pressure arrows 309 in FIG. 3) applies repetitive pressure against skin tissue 213 and fat tissue 220 and the associated vasculature, promoting blood flow and improved circulation from below skin ulcer 240. The interferential electrical stimulation is preferably applied simultaneously with the transmission of ultrasound waves by ultrasound apparatus 112, thereby further augmenting the circulation improvement induced by the ultrasound. It is believed that a periodic application of pressure pulses with alternating relief intermissions is preferred to a constant pressure application with respect to the tenability of living organic tissue, especially in circumstances of force accompanying an aggressive treatment. Accordingly, interferential electrical stimulation has been found to be effective for at least half an hour after an intensive ultrasound treatment, in accordance with the disclosed technique.

The operating parameters of the interferential electrical stimulation (e.g., intensity, frequency, pulse duration) may be varied over the course of a treatment session, such as in response to clinical feedback (e.g., an indication of pain or discomfort) from the patient. The operating intensity of the electrical stimulation is preferably between 5-90 mA. The interferential electrical stimulation may be performed using: premodulated, biphasic, interferential isoplanar (4 poles), interferential vectorial (4 poles), and medium frequency stimulation techniques, or combinations thereof, as known in the art. The interferential technique uses two alternating currents originating at different channels, each at slightly different carrier frequencies. The currents coincide at treatment region 230 and create interference (constructive or destructive), producing a resultant beat frequency equal to the difference between the actual frequencies provided by each pair of electrodes. For example, a frequency of 100 Hz is yielded by 3,900 Hz in one electrode pair and 4,000 Hz in the other electrode pair. Accordingly, the resultant wave is a 3,900-4,000 Hz carrier wave modulated at an envelope amplitude frequency of 100 Hz. The dominant carrier frequency depends on the geometrical locations of the electrodes. Interferential stimulation is almost exclusively delivered using a quadripolar technique, in which four independent pads are arranged in such a way as to achieve the desired effect. Typically, two pairs of electrodes are positioned around the treatment region, with each pair perpendicular to the other. Bipolar electrode placement may alternatively be used, in which the interference occurs within the electrical generator rather than within the tissues, thereby requiring only one pair of electrodes. The premodulated technique involves superimposing a signal with the effective frequency onto a continuously transmitted carrier wave, for instance, a 4000 Hz carrier wave modulated at an envelope amplitude frequency of 100 Hz. It is noted that multiple electrical stimulation techniques can be used, in various combinations, in various orders, and with various intermission durations (in between different electrical stimulation techniques), in accordance with the disclosed technique. For example, the electrical stimulation may include applying an IF vectorial technique initially for 10 minutes, then switching to an interferential technique for 5 minutes, then switching to a premodulated technique for an additional 5 minutes, then switching to a biphasic technique for another 10 minutes, then cycling back through this process again. According to another example, the electrical stimulation may include applying an interferential technique first for 8 minutes, then applying an IF vectorial technique for 2-3 minutes, then switching to the premodulated technique for 6 minutes, then to the biphasic technique for 7 minutes, then switching to the MF stimulation for 5-10 minutes then cycling back through this process again. It was found that interferential, IF isoplanar, IF vectorial, and premodulated techniques are preferable, with the IF vectorial technique being the most effective in terms of stimulating muscle contractions for applying pressure against the tissues and promoting blood flow in treatment region 230. While each interferential electrical stimulation technique is applied, the carrier wave frequency is preferably changed (hopped) at least once, thus preventing the body from adapting to the applied electrical stimulation (and consequently ceasing to react with intermittent muscle contractions), and avoiding the need to increase the operating intensity. For example, while each interferential electrical stimulation technique is applied, the carrier wave may be hopped from a 4,000 Hz carrier wave to a 2,400-2,500 Hz carrier wave. Similarly, the envelope or beat frequency (where relevant) is changed gradually or hopped between selected frequencies.

During the initial treatment session, it is preferable to use low current intensities in the range of approximately 3-5 mA, as a higher current intensity may agitate or alarm an inexperienced patient. In more advanced treatments, it is possible to apply the more effective higher current intensities in the range of approximately 5-90 mA. Patient feedback may be utilized by the treatment provider for adapting the operating intensity as necessary. The effective frequencies are between approximately 5-150 Hz. It is noted that intermittent muscle contractions may not occur when applying interferential electrical stimulation at operating frequencies above a certain level (e.g., approximately 250 Hz). At higher frequencies, the vibrations are so frequent that the muscles can remain constantly tense, whereas at lower frequencies the vibrations are slower but much stronger. Since the muscle adapts to a specific frequency, it is advisable to alter the operating frequency of the electrical stimulation throughout the duration of the treatment session, and even during the application of a particular stimulation technique. The operating frequency may be altered in an arbitrary manner, or in accordance with a predetermined pattern, such as: (1) applying a first frequency for a fixed amount of time before switching to a second frequency; (2) gradually changing frequencies from a first frequency to a second frequency, such as switching from 5 Hz to 150 Hz and back (e.g., in a sinusoidal cycle); (3) similar to pattern (2), but remaining for a longer duration (such as 1 second) at the extreme levels; (4) applying only the extreme frequencies intermittently. Other patterns for altering the operating frequency may also be employed.

Various operating parameters of the interferential electrical stimulation, such as: the frequency, amplitude modulated frequency, spectrum, rotation, emission, and pause parameters, are adjustable. The "frequency" parameter allows the operating frequency to be set between two available values (e.g., 2500 Hz or 4800 Hz) for each alternating current. The selection of the frequency value is crucial, since the interferential current penetrates more easily at a higher current frequency. The "amplitude modulated frequency (AMF)" can be chosen such that the basic value of the low frequency modulation can be set as needed. For example, the AMF parameter can be set to 100 Hz, but can be adjusted from 1 Hz to 100 Hz, with 1 Hz step intervals. The "spectrum" parameter can be used to adjust the AMF value, and is adjustable from 0 to 100 Hz, with 1 Hz step intervals. For example, at a setting of 100 Hz AMF and 50 Hz spectrum, the AMF will increase in the tissue from 100 Hz to 150 Hz and return again to 100 Hz. The spectrum parameter is used in order to avoid assuefaction symptoms. For the interferential vectorial technique, a quadripolar interferential current is employed, but the direction of the stimulation is the same as in the bipolar technique. Therefore, at a certain moment, the current is activated by only two diagonal electrodes. The tissue stimulation therefore rotates automatically between the electrodes. The "rotation" parameter can be used to manually adjust the rotation speed of the vector. The rotation parameter is usually assigned an arbitrary value between 1 and 100. The "emission" parameter allows for the adjustment of the stimulation length. The "pause" parameter enables the stimulation to be paused if necessary.

If the frequency or intensity of the interferential electrical stimulation is varied rapidly, then the frequency of the ultrasound transmission is preferably varied slowly. Conversely, if the frequency or intensity of the interferential electrical stimulation is varied slowly, then the frequency of the ultrasound transmission is preferably varied rapidly. In other words, it is suggested that the rate of varying the parameters related to the interferential electrical stimulation be inversely proportional to the rate of varying the parameters related to the ultrasound transmission.

Figure 5A:
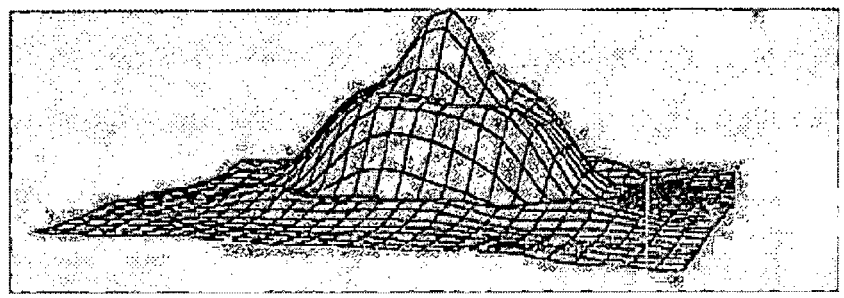
FIGS. 5A and 5B are three-dimensional graphical illustrations depicting the mountain-like morphing of tissues resulting from the synergy between interferential electrical stimulation and ultrasound waves applied to the treatment region, in accordance with an embodiment of the disclosed technique.
Figure 5B:
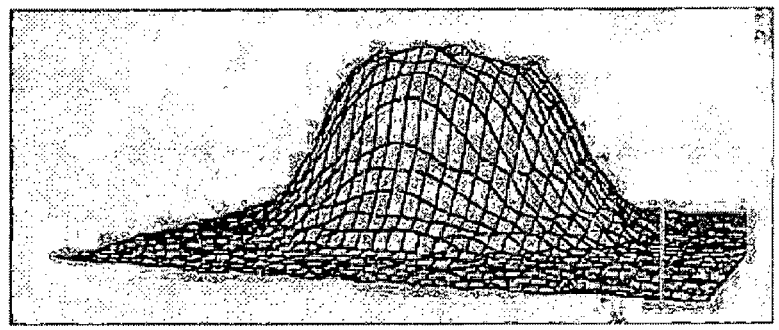

Reference is now made to FIGS. 5A and 5B, which are three-dimensional graphical illustrations depicting the mountain-like morphing of tissues resulting from the synergy between interferential electrical stimulation and ultrasound waves applied to the treatment region. The illustrations of FIGS. 5A and 5B are provided as examples of two stationary states between which the effected body tissue transitions. These morphologies and transitions result from intensity differential gradients that occur through the synergy between the altering interferential electrical stimulation and the transmitted ultrasound waves. When this synergy is applied beneath and around the treatment region, it provides physical and thermal stimulation with improved microcirculation in proximity to the skin ulcer, thus significantly assisting the body in healing the skin ulcer.

Figure 6:
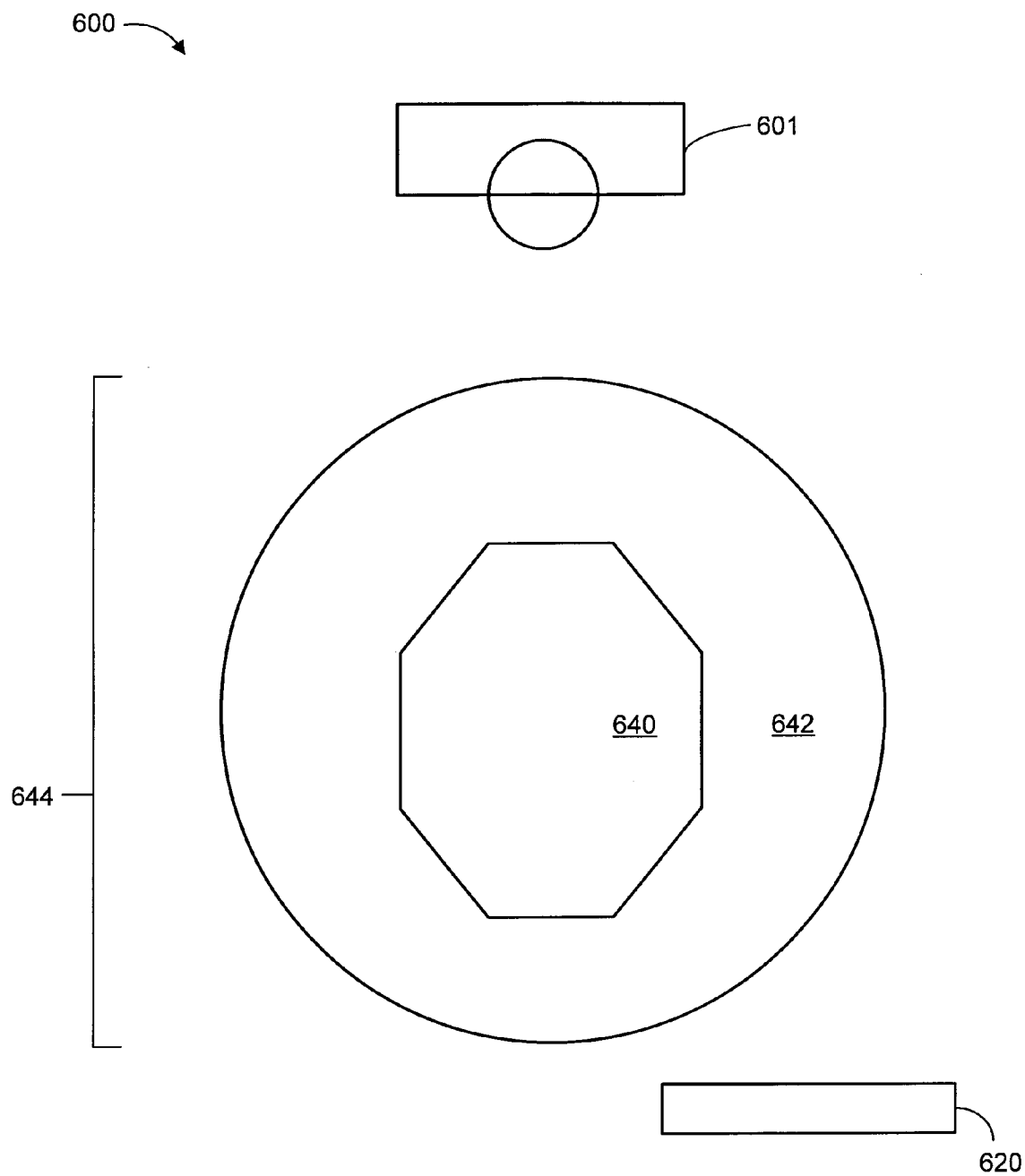
FIG. 6 is a schematic illustration of a measurement system for accurately measuring the size of the skin ulcer to be treated, constructed and operative in accordance with an embodiment of the disclosed technique.

Reference is now made to FIG. 6, which is a schematic illustration of a measurement system, generally referenced 600, for accurately measuring the size of the skin ulcer to be treated, constructed and operative in accordance with an embodiment of the disclosed technique. Measurement system 600 includes a camera 601, a reference measurement ruler 620, and a processor 622. Skin ulcer 644 includes a skin ulcer bed 640 and a peripheral skin ulcer region 642. Before beginning a treatment session according to the disclosed technique, it is recommended to obtain an accurate measurement of skin ulcer 644. The measurement is subsequently compared with similar measurements following successive treatment sessions, in order to quantitatively measure the progression of the healing of skin ulcer 644. A simple measurement of the length or width of skin ulcer 644 is insufficient, because skin ulcers are generally not uniform and do not heal in a uniform manner. A more accurate measurement of the healing progress of skin ulcer 644 involves measuring the respective surface areas of skin ulcer bed 640 and peripheral skin ulcer region 642. Reference measurement ruler 620 is positioned adjacent to skin ulcer 644, and an image of skin ulcer 644 is acquired using camera 601. Reference measurement ruler 620 includes measurement markings. A processor (not shown) receives the image, and assigns a pixilated scale to the distance between the measurement markings on reference measurement ruler 620. Once the scale is established, the processor analyzes the coloring of skin ulcer bed 640 and peripheral skin ulcer region 642, and calculates an accurate measurement for the respective surface areas by counting the number of pixels or each color and mapping the pixels to the scaled pixel size. In this manner, images of skin ulcer bed 640 and peripheral skin ulcer region 642 may be compared to prior such images, to allow an accurate quantitative determination of the healing progress of skin ulcer 644, irrespective of the exact type or development of the skin ulcer.

Referring back to FIGS. 1 and 2, during a treatment session in accordance with the disclosed technique, the treatment provider slowly, gradually and gently moves ultrasound transducer 212 over treatment region 230, while preferably gently executing small circular massaging motions with transducer 212. It is noted that the action of the treatment provider may be automated, such as by using a robot or machine. Ultrasound transducer 212 is forcefully but carefully applied to treatment region 230 to generate substantial pressure. It is noted that it is important to be gentle and attentive to any pain or discomfort experienced by the patient, as treatment region 230 may be very sensitive. The treatment provider may optionally provide local or systemic sedatives, in order to alleviate pain for the patient. Ultrasound transducer 212 is preferably designed to allow both a forceful massage action and the penetration of ultrasound waves 302 into the underlying tissue at treatment region 230. Preferably, the massaging action and forceful pressure applied to treatment region 230 by ultrasound transducer 212 is interspersed with periodic intermissions. Ultrasound transducer 212 may be tilted in different directions (e.g., left, right, front and back) over the course of the massaging. This is achieved by tilting and moving the wrist in different directions repetitively, for example left-right-left, front-back-front, and left-front-right-back (i.e, a circular motion using the wrist as opposed to a circular motion using the arm). In this manner, ultrasound waves 302 penetrate deeper into treatment region 230, as the surface area of the head of ultrasound transducer 212 in contact with the skin is made smaller by the tilting. The kneading motion, together with the pressure applied to the treatment region 230 by the head of transducer 210, presses and squeezes against the vasculature in the underlying tissues. For example, small circular massage motions can be interspersed with left-right-left tilting massage motions, or any combination of the above mentioned massage techniques, or other massage techniques known in the art. It is noted that the kneading action or the pressure exertion of the ultrasound transducer in accordance with the disclosed technique deviates from the general practice of ultrasound transmission for medical applications, which discourages any forceful contact between the ultrasound transducer and the skin.

A further measure to exert pressure on the treatment region is via a manual and/or mechanical external massage, such as by using massaging device 110. A practical and simple type of massage is the mere massaging by the bare hands of a treating person. However, various types of massaging tools or equipment are also applicable. Referring to FIG. 3, the massage applies pressure (as represented by arrows 314) against treatment region 230, thereby squeezing the skin surface and promoting blood flow to the area and improving the circulation and lymphatic network. Preferably, the massaging action is applied to the exact area of treatment region 230 on which ultrasound waves 320 are directed, simultaneously to the ultrasound transmission. The massage may be applied effectively during the ultrasound transmission or for a while thereafter.

According to another aspect of the disclosed technique, a gel 209 is rubbed onto skin layer 213 at treatment region 230 prior to the ultrasound transmission. Gel 209 is preferably water-based, to conform to the ultrasound conductive medium. Preferable gels can include ingredients such as: hydroxyl acids, plant extracts, wheat proteins, macadamia oil, chamomile, zinc, salicylic acid, and caffeine. Gel 209 has several purposes. Firstly, gel 209 effectively conducts ultrasound waves 302 between the ultrasound transducer 212 and the tissues at treatment region 230. Gel 209 is also designed to provide smooth penetration of the ultrasound waves 302 to the underlying tissues. In addition, gel 209 lubricates the skin and prevents friction and scrapes to the skin, especially in circumstances where the head of ultrasound transducer 212 is forcefully pressed or kneaded against treatment region 330. Also, drugs, active ingredients and antiseptics, if added to gel 209, are absorbed into and/or disinfect the epidermis layer (of skin tissue 213) more effectively because of ultrasound waves 302, the heated fluids and tissue material, and the appearance of ruptures or cracks in treatment region 230. This absorption is further enhanced by the head of ultrasound transducer 212 forcefully rubbing gel 209 against the skin. The drugs or active ingredients that are absorbed may promote blood flow and circulation, and provide the skin tissue with various beneficial minerals and nutrients, which may also substantially improve the skin appearance. Throughout the course of the treatment session, the massaging action involved in rubbing gel 209 onto the skin also serves to improve circulation and the operation of the lymphatic system at the treatment region 230.

The application of one or any combination of any of the pressure increasing measures detailed hereinabove (i.e., ultrasound wave transmission, ultrasound transducer kneading, interferential electrical stimulation, and external massaging), can exert sufficient and suitable pressure on treatment region 230 from opposite directions (e.g., from above and below the treatment region if the patient is in a supine position), which that contributes to an effective treatment. It was found that the more (and preferably all) of the pressure increasing measures that are applied, the more substantial and irrefutable are the improvement in blood flow and circulation. The ultrasound transducer kneading, the interferential electrical stimulation, and the external massage are preferably applied simultaneously with the ultrasound transmission.

It is appreciated that the improvement in blood flow resulting from the treatment of the disclosed technique also generally improves the circulatory system and metabolism processes at the treatment region. Due to the softening of tissues, the arteries and capillaries within these tissues become widened (i.e., vasodilation). Circulation is then accelerated, and the tissues receive more oxygen and nutrients. As a result, the circulatory system and lymphatic system reach healthier states. This in turn improves the healing process and tissue regeneration in the entire body, which further accelerates the healing process of skin ulcer 240.

The disclosed technique is applicable for treating different regions of the body, such as: feet, legs, thighs, hands, arms, buttocks, back, and the like. Ultrasound apparatus 112 and electrical stimulation apparatus 108 may be portable and may include different accessories, such as arm bands or leg bands, to enable ultrasound apparatus 112 and electrical stimulation apparatus 108 to fit snugly or tightly onto the treated body region. It is noted that a portable ultrasound apparatus and stimulation apparatus 108 may use a gel that is encased between the treatment region 230 and the ultrasound apparatus 112.

The system of the disclosed technique may be adapted for personal use by an individual, such as at his/her home or at any convenient location, without necessitating a visit to a clinic or office in order to be treated by another person. The duration of a treatment session in accordance with the disclosed technique generally varies from about 15 to 45 minutes.

Figure 7:
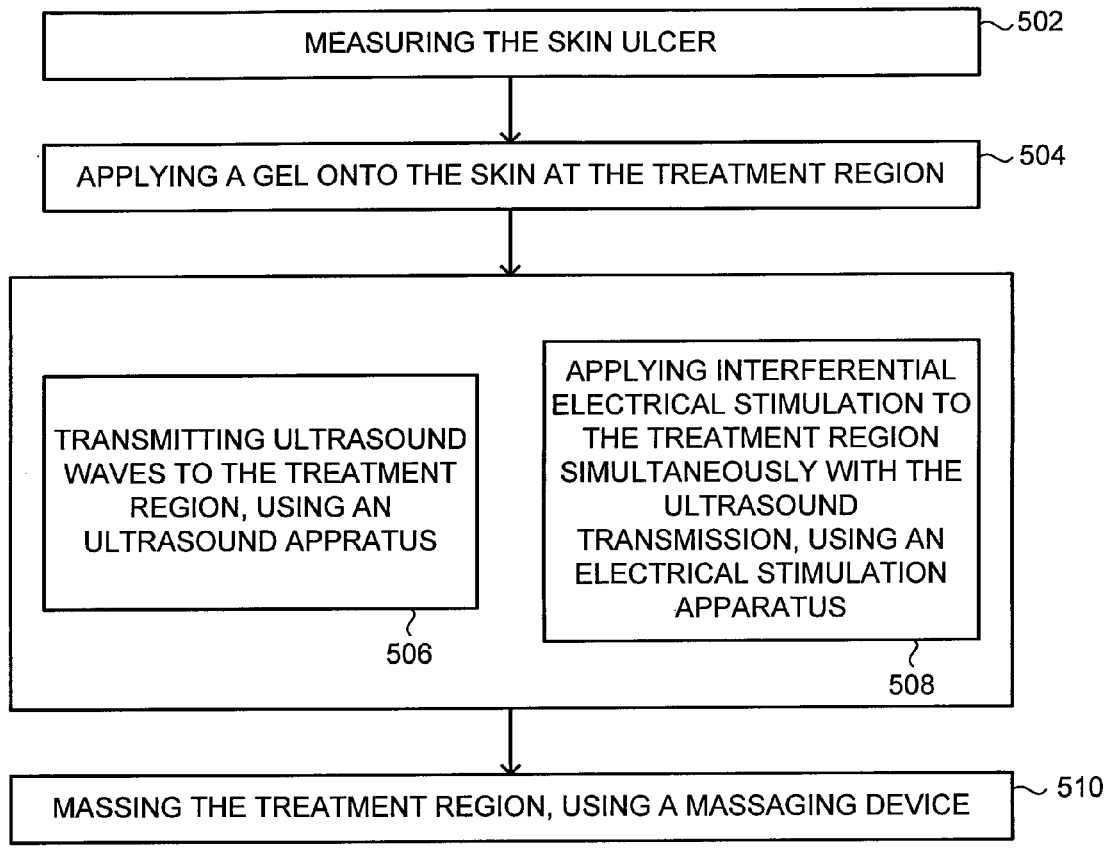
FIG. 7 is a flow diagram of a method for facilitating the healing of a skin ulcer, operative in accordance with an embodiment of the disclosed technique.

Reference is now made to FIG. 7, which is a flow diagram of a method for facilitating the healing of a skin ulcer, operative in accordance with an embodiment of the disclosed technique. In an optional procedure 502, the skin ulcer is measured. With reference to FIG. 6, measurement system 600 is employed to obtain accurate measurements of the respective surface areas of skin ulcer bed 640 and peripheral skin ulcer region 642. The measurements following successive treatment sessions are compared, to allow an accurate quantitative determination of the healing progress of skin ulcer 644, irrespective of the exact type or development of the skin ulcer.

In an optional procedure 504, a gel is applied onto the skin at the treatment region. With reference to FIG. 2, gel 209 is applied onto skin layer 213 at treatment region 230. Gel 209 serves to enhance the penetration of ultrasound waves 302 to the underlying tissues, to lubricate the skin and prevent friction by the kneading action of ultrasound transducer 212, and/or to enable the absorption of active ingredients into the skin (e.g., for improving circulation and/or for transmitting beneficial nutrients to the skin tissue).

In procedure 506, ultrasound waves are transmitted to the treatment region using an ultrasound apparatus. With reference to FIGS. 1, 2 and 3, ultrasound transducer 212 of ultrasound apparatus 112 transmits ultrasound waves 302 toward treatment region 230 that includes a skin ulcer 240. Preferably, ultrasound transducer 212 simultaneously massages treatment region 230, such as by executing a kneading motion, while transmitting ultrasound waves 302.

In procedure 508, interferential electrical stimulation is applied to the treatment region simultaneously with the ultrasound transmission, using an electrical stimulation apparatus. With reference to FIG. 2, electrodes 208 are positioned onto treatment region 230, and an interferential current is applied via electrodes 208, to stimulate intermittent contractions of muscle tissue 216. The contracting muscles repeatedly press against skin tissue 213 and fat tissue 220, promoting blood flow and improved circulation below skin ulcer 240 and facilitating the healing process.

In an optional procedure 510, the treatment region is massaged using a massaging device. Referring to FIG. 2, massaging device 110 massages and applies pressure to treatment region 230, further promoting blood flow and improved circulation in skin tissue 213 and fat tissue 220 in proximity to skin ulcer, and further facilitating the healing process. The massage is preferably applied simultaneously to the ultrasound transmission and electrical stimulation, but may alternatively be applied afterwards. Further preferably, the massage and/or interferential electrical stimulation are performed both during and after the ultrasound transmission. For such a treatment session, the post-ultrasound stage of massaging and electrical stimulation (procedures 508 and 510) is performed for about 20-30 minutes, following the initial 45 minutes in which the ultrasound transmission, massaging and electrical stimulation (procedures 506, 508 and 510) are applied together.

It will be appreciated by persons skilled in the art that the technique is not limited to what has been particularly shown and described hereinabove.

The invention claimed is:

1. A method for facilitating healing of a skin ulcer on a treatment region of a body, the method comprising:
   measuring size of the skin ulcer;
   applying a gel onto skin at the treatment region;
   transmitting ultrasound waves to the treatment region;
   positioning electrodes of an electrical stimulation apparatus onto the skin at the treatment region in proximity to the skin ulcer;
   applying interferential electrical stimulation through the electrodes to the treatment region simultaneously with transmission of the ultrasound waves; and
   massaging the treatment region simultaneously with transmitting ultrasound waves and applying interferential electrical stimulation.

2. The method according to claim 1, wherein measuring size of the skin ulcer comprises:
   positioning a reference measurement ruler adjacent the skin ulcer;
   imaging the skin ulcer and the reference measurement ruler; and
   calculating at least one measurement of a surface area of a skin ulcer bed and a surface area of a skin ulcer region based on a comparative reference scale established using the reference measurement ruler.

3. The method according to claim 1, further including quantitating healing progression of the skin ulcer, the quantitating comprising:
   measuring the skin ulcer before beginning a treatment session by calculating at least one measurement of a surface area of a skin ulcer bed and a surface area of a skin ulcer region; and
   comparing measurements of the surface areas calculated following successive treatment sessions.

4. The method according to claim 1, wherein the ultrasound waves are transmitted to the treatment region at an operating frequency between 1 and 3 MHz and at an operating intensity between 1.5-2.1 $W/cm^2$.

5. The method according to claim 1, wherein an operating frequency of the interferential electrical stimulation is varied during a treatment session, the varying in accordance with a predetermined pattern selected from the group consisting of:
   applying a first frequency for a fixed amount of time before switching to a second frequency;
   gradually changing frequencies from a first frequency to a second frequency over various durations of time; and
   intermittently applying extreme frequencies within a frequency range.

6. The method according to claim 1, wherein the method does not comprise applying a vacuum or suction.

* * * * *